US00PP33900P2

(12) United States Plant Patent
Ranney et al.

(10) Patent No.: US PP33,900 P2
(45) Date of Patent: Jan. 25, 2022

(54) AZALEA PLANT NAMED 'NCRX5'

(50) Latin Name: ***Rhododendron* hybrid**
Varietal Denomination: NCRX5

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/343,083

(22) Filed: Jun. 9, 2021

(51) Int. Cl.
*A01H 5/02* (2018.01)
*A01H 6/36* (2018.01)

(52) U.S. Cl.
USPC ..... Plt./238
CPC ..... *A01H 6/364* (2018.05)

(58) Field of Classification Search
USPC ..... Plt./238
CPC ..... A01H 5/02
See application file for complete search history.

(56) References Cited

PUBLICATIONS https://plantaddicts.com/perfecto-mundo-double-white-azalea; May 18, 2021; 4 pages.*
https://www.google.com/search?q=Rhododendron+Perfecto+Mundo+Double+White&rlz=1C1GCEB_enUS773&biw=1536&bih=754&ei=dMwEYd6GF_Og5NoProqNkAQ&oq=Rhododendron+Perfecto+Mundo+Double+White&gs_lcp=Cgdnd3Mtd216EANKBQhAEgExSgQIQRgBUNMjWNMjYJAtaAFwAHgAgAE7iAFxkgEBMpgBAKABAcABAQ&sclient=gws-wiz&ved=0ahUKEwjekOvFt4zyAhVzEFkFHS5.*
FA0IQ4dUDCA4&uact=5; Jul. 31, 2021; 1page.*

* cited by examiner

*Primary Examiner* — Kent L Bell
(74) *Attorney, Agent, or Firm* — Cassandra Bright

(57) ABSTRACT

A new and distinct cultivar of *Rhododendron* plant named 'NCRX5' having a profusion of large, double white flowers with a yellow-green blotch, cold-hardiness in USDA Zone 6b, consistent reblooming in Fall, dense habit, and a tetraploid cytotype. The new cultivar is a *Rhododendron*, suitable for ornamental garden purposes.

2 Drawing Sheets

Latin name of the genus and species: The Latin name of the novel plant variety disclosed herein is *Rhododendron* hybrid.

Variety denomination: 'NCRX5'.

The inventive hybrid was selected from oryzalin-treated seedlings derived from a controlled cross between evergreen azaleas *Rhododendron* 'Girard's Pleasant White' (unpatented) and *Rhododendron* 'Mootum' (patented: U.S. Plant Pat. No. 18,416; Autumn Moonlight®). Prior to the designation of the varietal denomination, 'NCRX5' was referred to by its experimental code: H2009-235-008. 'NCRX5' is a stable tetraploid cytotype.

BACKGROUND OF THE INVENTION

The present invention comprises a new and distinct hybrid evergreen azalea cultivar hereinafter referred to by the cultivar name 'NCRX5'. This hybrid azalea was developed via a controlled breeding program in Mills River, N.C. 'NCRX5' was selected for its prolific, large, double white flowers, moderate and dense growth habit, and consistent fall reblooming. 'NCRX5' was obtained from the controlled, hand pollination of emasculated, female *Rhododendron* 'Girard's Pleasant White' (unpatented) and pollen parent *Rhododendron* 'Mootum' (patented: U.S. Plant Pat. No. 18,416; Autumn Moonlight®). Seedlings from these controlled pollinations were then treated with a mitotic inhibitor (oryzalin) to develop a population of stable tetraploid azaleas. 'NCRX5' was selected after 8 years in field and container trials at a research center in Mills River, N.C. Container trials were conducted using pine bark media supplemented with 1.04 kg·m-3 dolomitic lime, 0.74 kg-m-3 granulated and top-dressed with 5- to 6-month slow-release fertilizer. Full-sun field trials were conducted in plastic-covered, bark-amended clay soils with minimum winter temperatures of −2° F. (−19° C.) and maximum summer temperatures 98° F. (37° C.). The first asexual propagation of 'NCRX5' occurred in 2011 by rooting stem cuttings at a research nursery in Mills River, N.C. 'NCRX5' roots readily from firm softwood cuttings treated with a basal dip of 3,000-5,000 ppm indole-butyric acid (potassium salt) in water. 'NCRX5' has been found to retain its distinctive characteristics through successive asexual propagations over 10 years.

Genome size and ploidy level were determined via flow cytometry, following the methods described in Jones et al., 2007, using the internal standard *Pisum sativum* 'Ctirad' and DAPI (4', 6-Diamidino2-phenylindole) fluorochrome. 'NCRX5' was found to have a genome size of approximately 2.6 pg indicating a tetraploid cytotype. This is approximately two times the size of diploid cytotypes. Ploidy levels and relative genome sizes of diverse species, hybrids, and cultivars of *Rhododendron*. Journal of the Amerierican *Rho-*

*dodendron* Society 61(4):220-227. Jones, J. R., T. G. Ranney, N. P. Lynch, and S. L. Krebs. 2007.

SUMMARY OF THE INVENTION

The following are the unique combination of characteristics of this new cultivar when grown under standard horticultural practices at a research nursery in Mills River, N.C.

1. Profusion of large, double, white flowers with a yellow-green blotch.
2. Cold hardy to USDA Zone 6b.
3. Dense, compact habit.
4. Consistent reblooming in fall.
5. Tetraploid cytotype.

TABLE 1

COMPARISON WITH PARENTS

| Plant | Flower Color and Type | Characteristics |
|---|---|---|
| FEMALE: *Rhododendron* 'Girard's Pleasant White'(unpatented) | White Single | Hardiness: USDA Zone 5<br>Mature Height × Width: 60 cm × 60-90 cm<br>Ploidy: Diploid.<br>Petal number: 5 |
| MALE: *Rhododendron* 'Mootum' (U.S. Plant Pat. No.18,416) | White Double | Hardiness: USDA Zone 7<br>Mature Height × Width: 150 cm × 120 cm<br>Ploidy: Diploid.<br>Flower size: 6.35 cm -7 cm.<br>Petal Number: 10-15. |
| *Rhododendron* 'NCRX5' | White, double flowers with a yellow-green blotch. | Hardiness: USDA Zone 6B<br>Mature Height × Width: 75 cm-100 cm × 100 cm-120 cm.<br>Ploidy: Tetraploid.<br>Flower size: 7 cm -9 cm.<br>Petal number: 10-12. |

TABLE 2

COMPARISON WITH COMMERCIAL CONTROLS

| Plant | Flower Color and Type | Habit | Additional characters |
|---|---|---|---|
| *Rhododendron* 'Robleg' (U.S. Plant Pat. No. 15,227) | White, single flowers with a yellow-green blotch. | Mid-sized/large: 120 cm-150 cm × 20 cm-120 cm. | Hardy to Zone 7 Diploid |
| *Rhododendron* 'Robley' (U.S. Plant Pat. No. 25,046) | White (RHS White Group 155B-D), single flowers lacking yellow-green blotch. | Compact: 75 cm × 90 cm. | Hardy to Zone 7 Diploid |
| *Rhododendron* 'NCRX5' | White, double flowers with a yellow-green blotch. | Mid-sized: 75 cm to 100 cm-120 cm. | Hardy to Zone 6b Tetraploid |

BRIEF DESCRIPTION OF THE DRAWINGS

'NCRX5' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

DETAILED BOTANICAL DESCRIPTION

Figure 1:
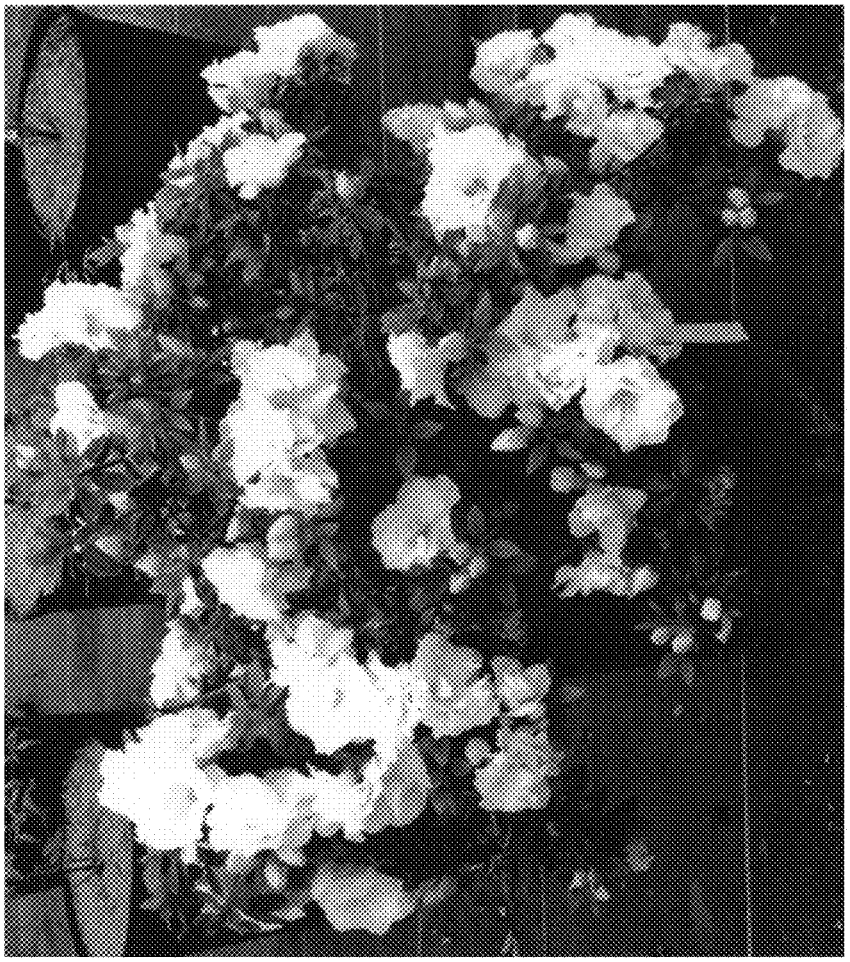
FIG. 1: Image showing dense plant habit and form and floriferousness of a 3-year-old container-grown plant in Grand Haven, Mich., in 2020.
Figure 2:
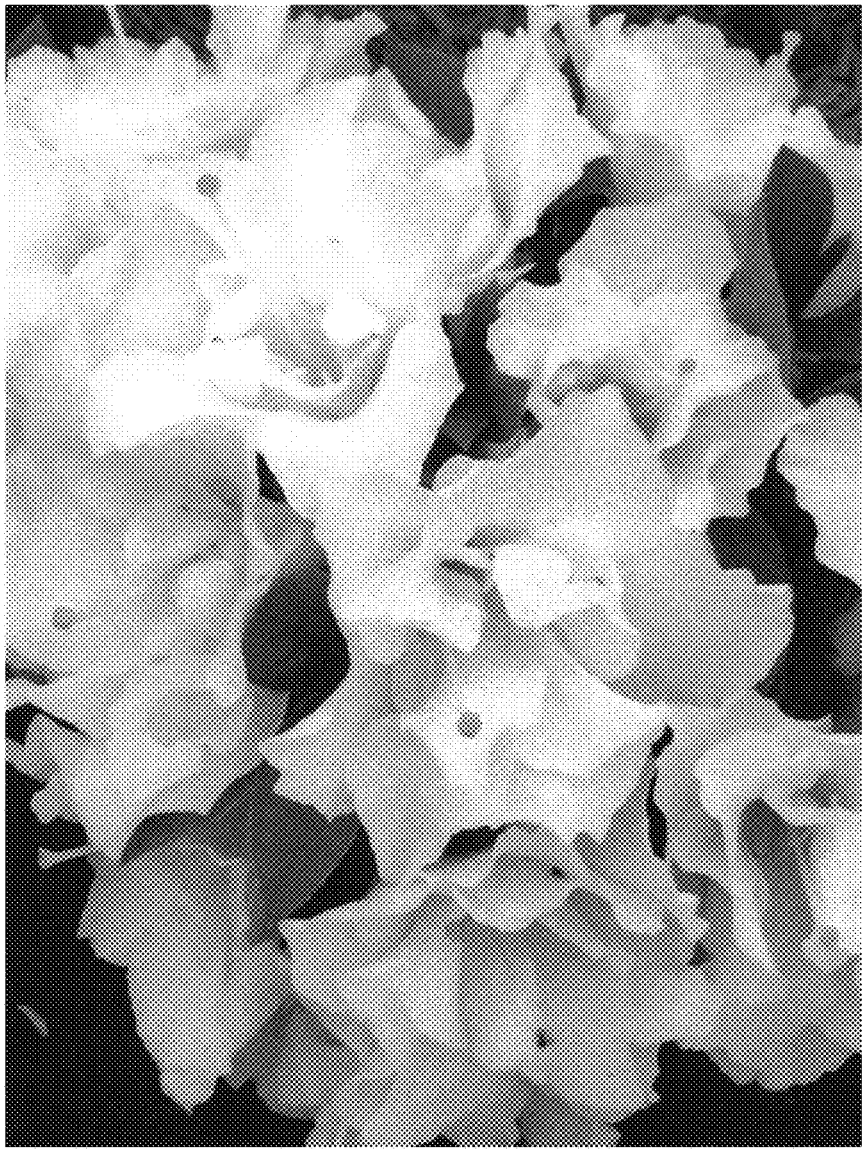
FIG. 2: Image showing fully expanded trusses with large, double white flowers on a 2-year-old container plant grown in Grand Haven, Mich., in 2020.

The following is a detailed description of the botanical characteristics of the new and distinct hybrid evergreen azalea known by the denomination 'NCRX5'. The detailed description was taken on a 3-year-old container-grown plant in Mills River, N.C., in 2020. Data was supplemented by observations/measurements taken on a 5-year-old individual located in field trials in Mills River, N.C., as well as information provided from cooperators in Grand Haven, Mich. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

Plant:

*Plant type*.—Evergreen flowering shrub.
*Growth habit/form*.—Globose.
*Height at maturity*.—75 cm-100 cm.
*Width at maturity*.—100 cm-120 cm.
*Roots*.—Fibrous. Tan, not accurately measured with R.H.S. chart.
*Growth rate*.—Moderate.

Shoots and branches:

*Shoots* (*softwood new growth*).—Shape: Rounded. Color: RHS Yellow-Green Group 147D. Texture: Pubescent. Pubescence color: RHS Greyed-Orange Group 147D. Shoot diameter: Approximately 2-3 mm. Shoot length: Variable, ranging from approximately 12 cm-20 cm. Internode length: Approximately 3 cm-5 cm.

*Shoots* (*prior year's woody shoots*).—Shape: Rounded. Color: Greyed-Orange Group 164B with small exfoliating streaks and sections (RHS Greyed-Orange Group 165A and 165B). Stem diameter: About 2 mm-5 mm. Stem length: Variable, ranging from about 6-20 cm. Stem aspect: 0-90°. Texture: Pubescent.

*Branches*.—Shape: Rounded. Color: RHS Greyed-Orange Group 166A with exfoliating sections (RHS Greyed-Orange Group 165B). Texture: Gently exfoliating. Branch diameter: Variable, ranging from about 5-10 mm. Branch length: Variable, ranging from about 10 cm to 30 cm. Branching: Freely branched. Number of lateral branches: Approximately 30-50.

Foliage:

*Type*.—Evergreen.
*Arrangement*.—Alternate.
*Division*.—Simple.
*Shape*.—Elliptic to obelliptic.
*Apex*.—Mucronate.
*Base*.—Cuneate.
*Margin*.—Entire, ciliate in some instances.
*Venation*.—Reticulate.
*Leaf internode length*.—Approximately 3 mm-8 mm.
*Immature leaf*.—

*Adaxial (upper) surface.*—
*Color.*—RHS Yellow-Green Group 146B.
*Surface.*—Lightly pubescent.
*Pubescence color.*—RHS White Group NN155B.
*Abaxial (lower) surface.*—
*Color.*—RHS Yellow-Green Group 146D.
*Surface.*—Pubescent along midrib.
*Pubescence.*—RHS White Group NN155B.
*Mature leaf.*—
*Length.*—Approximately 2.5-4 cm.
*Width.*—Approximately 1-2 cm.
*Color.*—
*Adaxial (upper) surface.*—RHS Green Group NN137A.
*Abaxial (lower) surface.*—RHS Green Group 138B.
*Surface.*—Both sides are lightly pubescent.
*Pubescence color.*—RHS Greyed-Orange Group 167C. Fall/winter color Adaxial side.—RHS Yellow-Green Group 146A. Abaxial side.—RHS Yellow-Green Group 146D.

Petiole:
*Shape.*—Lunate.
*Length.*—Approximately 6-10 mm.
*Width.*—Approximately 1-2 mm.
*Color.*—
*Adaxial side.*—RHS Yellow-Green Group 144C.
*Abaxial side.*—RHS Yellow-Green Group 144B.
*Surface.*—Both sides are pubescent.
*Pubescence color.*—RHS Greyed-Orange Group 167C.

Flower:
*Type.*—Congested terminal raceme (truss).
*Flowering season.*—Mid-Spring (Mid-April to June). Consistently reblooms in Early Fall (Late September to late October).
*Flowering habit.*—Free-flowering.
*Flowers per truss.*—3-5.
*Consistency in display.*—Blooms reliably in the Spring and consistently reblooms in the Fall.
*Lastingness of flowers.*—Each flower lasts approximately 3-7 days.
*Fragrance.*—None.
*Self-cleaning or persistent.*—Persistent.

Truss bud:
*Length.*—About 10 mm-16 mm.
*Diameter.*—About 6 mm-10 mm.
*Bud scales.*—Number: Variable: 3-7; 4 is average. Length: Approximately 10 mm-18 mm. Width: Approximately 5 mm-11 mm. Color prior opening: RHS Yellow-Green Group 146B to RHS Green-White Group 157B. Color after flowers emerge: Bud scales fade to RHS Yellow-White Group 158A Texture: Adaxial side: Smooth. Abaxial side: Pubescent at tip. Color: RHS Greyed-Orange Group 165B.

Emerging flowers prior to opening:
*Shape.*—Elliptic, acuminate.
*Length.*—2-3 cm.
*Diameter.*—13.5 mm-19 mm.
*Color.*—RHS White Group NN155 B and NN155C fading to RHS Yellow-Green 144C at base.

Perianth:
*Diameter at anthesis.*—7 cm-9 cm.
*Depth.*—3.5 cm-5 cm.
*Organization.*—Petals and petaloids are arranged in two whorls.
*Aspect.*—Facing upwards and outwards.
*Shape.*—Broadly funnel-shaped.
*Attachment.*—Pedicellate.

Petals:
*Length.*—Outer whorl: 6.5 cm-8.5 cm. Inner whorl/Petaloids: 3.5 cm-5.5 cm.
*Width.*—Outer whorl: 3 cm-4 cm. Inner whorl/Petaloids: 1.5 cm-3.5 cm.
*Shape.*—Obovate.
*Apex.*—Obtuse.
*Base.*—Acuminate
*Margin.*—Undulate.
*Fused or unfused.*—Fused at the midpoint.
*Number.*—10-12.
*Color.*—Color is consistent from opening to anthesis and between petals and petaloids. Adaxial (upper) surface: RHS White Group NN155 B, NN155C, NN155D. Blotch: RHS Yellow-Green 150C, sometimes RHS Yellow-Green 145C. Surface: Smooth, silky. Abaxial (lower) surface: RHS White Group 155B, 155C, 155D. Surface: Smooth, silky.

Calyx/receptacle:
*Shape.*—Star-shaped, single-whorl of persistent sepals.
*Sepals.*—Number: 5. Length: 6 mm-9 mm. Width: 2 mm-4 mm. Shape: Lanceolate. Apex: Acuminate. Margin: Entire, ciliate. Color: RHS Yellow-Green Group 148C. Surface: Pubescent. Pubescence color: RHS Greyed-Orange Group 165C.

Pedicels:
*Shape.*—Rounded.
*Length.*—Approximately 5 mm-15 mm.
*Diameter.*—Approximately 2 mm-5 mm.
*Color.*—RHS Yellow-Green Group N148C.
*Surface.*—Pubescent.
*Color.*—RHS Green Group 143C.

Reproductive organs:
*Reproductive organs.*—Reproductive characters, especially anther length, stamen number, and anther dimensions can be highly variable. Some flowers exhibit stunted styles, filaments, and/or anthers.

Gynoecium:
*Pistil number.*—0-1.
*Pistil length.*—4 cm-5.5 cm.
*Pistil diameter.*—0.5 mm-0.7 mm.
*Stigma shape.*—Orbicular to elliptic; flat.
*Stigma length.*—1 mm-2 mm.
*Stigma width.*—1 mm-2 mm.
*Stigma color.*—RHS Yellow-Green Group 151D.
*Style color.*—RHS White Group NN155C.
*Ovary shape.*—Dome-shaped.
*Ovary length.*—Approximately 5 mm-6 mm.
*Ovary diameter.*—Approximately 3 mm-4 mm.
*Ovary color.*—RHS Yellow-Green Group 147B (under pubescence).
*Surface.*—Pubescent.
*Color.*—RHS White Group 155A.

Androecium:
*Stamen number.*—0-7.
*Anther shape.*—Ovoid with two apical pores.
*Anther attachment.*—Dorsifixed. Production of fully formed filaments and anthers is rare.

Other characteristics:
Propagation: Roots readily (>90%) from firm, terminal, softwood stem cuttings taken in mid-summer. 'NCRX5' roots well when the bottom 2 cm of the stems are treated for 5 seconds with 3,000-5,000 ppm of potassium salt indole-3-butyric acid (KIBA) dissolved in water and placed under intermittent mist for 8-10 weeks until roots form.

Disease and insect resistance: No significant disease or insect pests have been observed.

Cold hardiness: Has been reliably cold hardy in USDA 6b. Has not been evaluated in colder climates.

Ploidy: 'NCRX5' is a stable tetraploid. 'NCRX5' has been confirmed via flow cytometry and remains stable after successive propagation.

Fruit/seed:

*Fruit type*.—Capsule.

*Fruit texture*.—Pubescent.

*Fruit length*.—Approximately 5-6 mm.

*Fruit diameter*.—Approximately 3-4 mm.

*Fruit color*.—Immature: RHS Yellow-Green Group 147B. Mature: RHS Greyed-Orange Group N167A.

*Seed number*.—Seed is rarely produced.

*Seed length*.—Approximately 1 mm.

*Seed diameter*.—Approximately 0.5 mm.

*Seed color*.—RHS Greyed-Orange Group 164A.

What is claimed is:

1. A new and distinct cultivar of *Rhododendron* plant named 'NCRX5' as herein illustrated and described.

* * * * *